United States Patent [19]

Coates et al.

[11] Patent Number: 5,254,698

[45] Date of Patent: Oct. 19, 1993

[54] PHENYLDIOXANES

[75] Inventors: David Coates, Wimborne; Simon Greenfield; Graham Smith, both of Poole, all of Great Britain; Volker Reiffenrath, Rossdorf, Fed. Rep. of Germany; Joachim Krause, Dieburg, Fed. Rep. of Germany; Herbert Plach, Darmstadt, Fed. Rep. of Germany

[73] Assignee: Merck Patent Gesellschaft mit beschrankter Haftung, Darmstadt, Fed. Rep. of Germany

[21] Appl. No.: 654,607

[22] PCT Filed: Dec. 8, 1990

[86] PCT No.: PCT/EP90/02132

§ 371 Date: Feb. 12, 1991

§ 102(e) Date: Feb. 12, 1991

[87] PCT Pub. No.: WO91/09026

PCT Pub. Date: Jun. 27, 1991

[30] Foreign Application Priority Data

Dec. 8, 1989 [GB] United Kingdom ............... 8927778
Dec. 19, 1989 [GB] United Kingdom ............... 8928583

[51] Int. Cl.$^5$ ............................................. C07C 319/06
[52] U.S. Cl. ..................................... 549/369; 549/374; 549/375; 252/299.61
[58] Field of Search ........................ 549/369, 374, 375

[56] References Cited

U.S. PATENT DOCUMENTS 4,621,901 11/1986 Petrzilka et al. .................. 549/369
4,846,998 7/1989 Pohl et al. ........................ 549/369
4,871,469 10/1989 Reiffenrath et al. .............. 549/369

Primary Examiner—C. Warren Ivy
Assistant Examiner—Raymond Covington
Attorney, Agent, or Firm—Millen, White, Zelano & Branigan

[57] ABSTRACT

Phenyldioxanes of the formula I

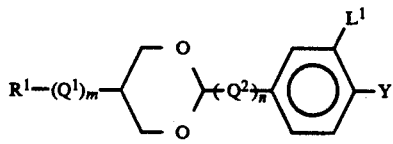

wherein
$R^1$ is an alkyl or alkenyl residue each with up to 16 C atoms, wherein one or two non-adjacent $CH_2$ groups of these residues may be replaced by —CO—O— or —O—CO—,
$Q^1$ and $Q^2$ are each independently

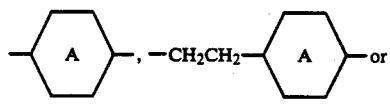

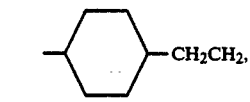

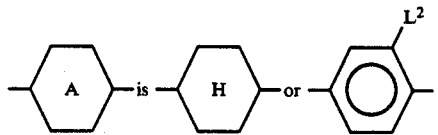

$L^1$ and $L^2$ are each independently F or H, and
Y is Cl, F, CN, $CF_3$, $OCF_3$ or $OCF_2H$,
m and n is 0 or 1,
are suitable as components of liquid crystal media.

10 Claims, No Drawings

PHENYLDIOXANES

The invention relates to Phenyldioxanes of the formula I $$R^1-(Q^1)_m-\underset{O}{\underset{|}{\overset{O}{\overset{|}{\diagup}}}}\hspace{-2pt}\diagdown Q^2)_n-\underset{}{\underset{}{\overset{L^1}{\bigcirc}}}-Y \qquad I$$

wherein
$R^1$ is an alkyl or alkenyl residue each with up to 16 C atoms, wherein one or two non-adjacent $CH_2$ groups of these residues may be replaced by —O—, —S—, —CO—O— or —O—CO—,
$Q^1$ and $Q^2$ are each independently $-\langle A \rangle-$, $-CH_2CH_2-\langle A \rangle-$ or $-\langle A \rangle-CH_2CH_2$, $-\langle A \rangle-$ is $-H-$ or $-\overset{L^2}{\bigcirc}-$ $L^1$ and $L^2$ are each independently F or H, and
Y is Cl, F, CN, $CF_3$, $OCF_3$ or $OCF_2H$,
m and n are 0 or 1
with the provisos that
a) in the case m and n are O, $L^1$ is F and Y is Cl, F, —$CF_3$, —$OCF_3$ or $OCF_2H$ or $L^1$ and $L^2$ are H and Y is Cl or F.
b) in the case that n is O, m is 1 and $Q^1$ is $-\langle A \rangle-$ one of $L^1$ and $L^2$ is F and Y is Cl, F, $CF_3$, $OCF_3$ or $OCF_2H$, and
c) in the case that n is 1 and m is O and $Q^2$ is $-\langle A \rangle-$ one of $L^1$ and $L^2$ is F or $L^1$ and $L^2$ are H and Y is Cl, —$CF_3$, —$OCF_3$ or —$OCF_2H$.

The compounds of the formula I can be used as components of liquid crystal media, in particular for displays which are based on the principle of the twisted nematic cell, including TN cells with a higher twist angle like STN, SBE, OMI etc., on the guest-host effect on the effect of deformation of orientated phases or on the effect of dynamic scattering.

Compounds similar to those of formula I are known from DE 29 44 905. These compounds comprising 2 rings but no terminal chlorine tend to reduce the mesophase range.

JP-57 064 689 describes $$R-\underset{O}{\underset{|}{\overset{O}{\overset{|}{\diagup}}}}\hspace{-2pt}\diagdown-\bigcirc-\bigcirc-F.$$

Compounds of the formula I with three rings and L=H or F are claimed in EP 0 087 679 and EP 0 154 840 via a very broad formula. There are, however, no specific examples for these compounds so that it may be stated that the surprisingly advantageous properties of these compounds have neither been realized nor used.

Similar phenyldioxanes with terminal $OCF_3$-group but without ethyllinhage are known from WO 89 02 884.

WO 87/06602 describes $$R-\underset{O}{\underset{|}{\overset{O}{\overset{|}{\diagup}}}}\hspace{-2pt}\diagdown-\bigcirc-CF_3$$

and
WO 90/01056 describes $$R-\underset{O}{\underset{|}{\overset{O}{\overset{|}{\diagup}}}}\hspace{-2pt}\diagdown-\bigcirc-OCF_2H.$$

Furthermore ethyl-linked phenyldioxanes with a negative or neutral value of the dielectricity are known:

$$R^1-\underset{O}{\underset{|}{\overset{O}{\overset{|}{\diagup}}}}\hspace{-2pt}\diagdown-CH_2CH_2-\bigcirc-\bigcirc-R^2$$

EP-0 154 840.
The invention was based on the object of discovering new stable liquid crystalline or mesogenic compounds which are especially suitable for active matrix displays without exhibiting the shortcomings of the prior art compounds.

Surprisingly, it has been found that the compounds according to formula I meet these criteria to an outstanding degree and allow the realization of a very high resistivity and simultaneously favorable electro-optic characteristics. These compounds also show a surprisingly good solubility at −20° C. in many LC base materials from other compound classes.

By providing the compounds of the formula I, the range of liquid crystal substances which are suitable, under various technological aspects for the preparation of nematic mixtures is also quite generally widened considerably.

The compounds of the formula I have a wide field of application and they are preferably added to liquid crystal base materials from other classes of compounds, for example in order to increase the clearing point while having little effect on other physical properties.

The compounds of the formula I are colourless in the pure state and form liquid crystal mesophases in a temperature range which is favorably placed for electro-optical use. They are sufficiently stable towards chemicals, heat and light.

The invention thus relates to the compounds of the formula I in particular to the compounds of the formula I1,

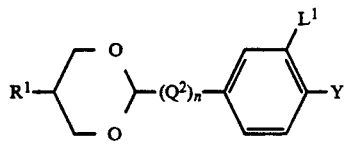

wherein $R^1$, $Q^2$, $L^1$ and Y have the meaning given and Y is Cl or in the case that one of $L^1$ and $L^2$ is F also F, in particular, wherein $Q^2$ is 1,4-phenylene and n is 1 and Y is Cl, and furthermore to the compounds of the formula I2

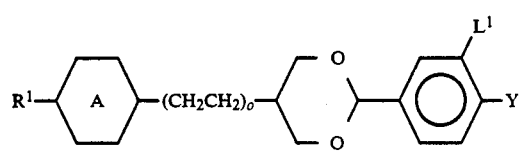

wherein $R^1$, $L^2$ and Y have the meaning given o is 0 or 1, and

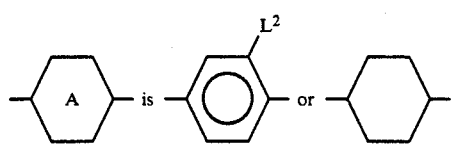

with the proviso that in the case that o is O Y is different form CN and one of $L^1$ and $L^2$ is F.

Furthermore the invention relates to the use of these compounds as components of liquid crystal media. The invention furthermore relates to liquid crystal media containing at least one compound of the formula I and to liquid crystal display elements, in particular electro-optical display elements, which contain media of this type.

The compounds of the formula I are in particular suitable as compounds of liquid crystal media for displays which are based on the principle of polymer dispersed (pdlc) or polymer network (pn) liquid crystals due to their favorable optical anisotropy and their dielectric anisotropy.

Above and below $R^1$ has the mentioned meaning, unless expressly stated otherwise.

The compounds of the formula I1 accordingly include compounds of the part formulae I1a to I1h:

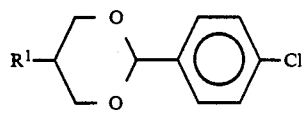
I1aa

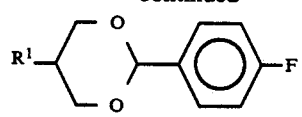
I1ab

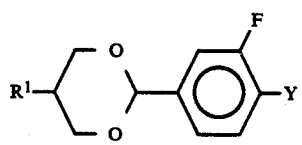
I1b

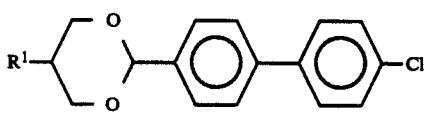
I1c

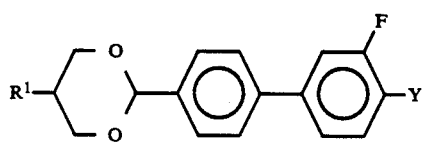
I1d

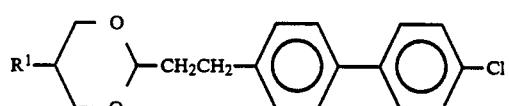
I1e

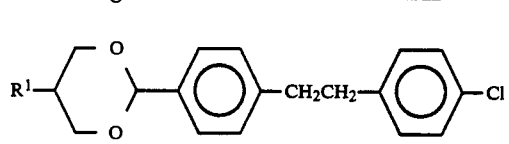
I1f

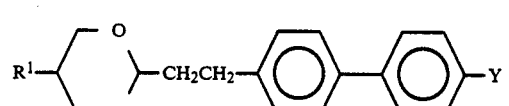
I1g

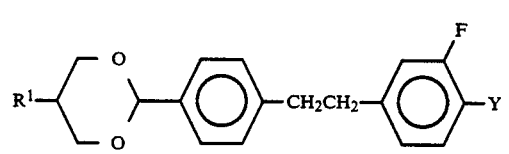
I1h

The compounds of the formulae I1c and I1d are particularly preferred.

The compounds of the formula I2 include ethyl-linked phenyldioxanes of the formula I2a to I2f:

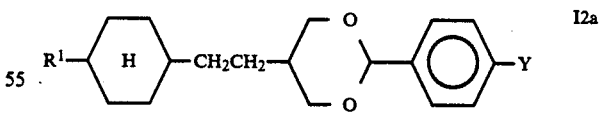
I2a

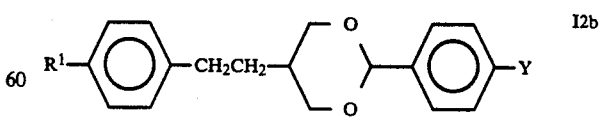
I2b

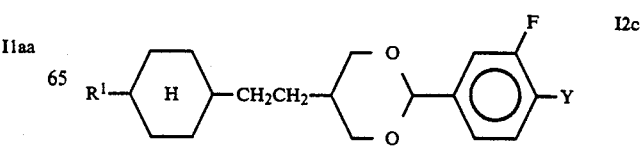
I2c

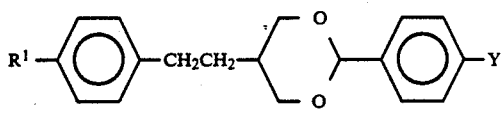

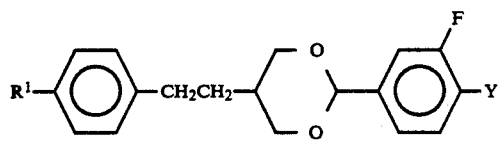

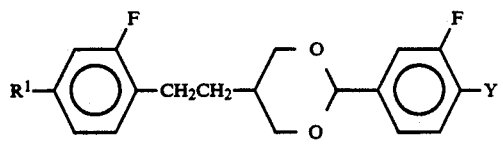

Y is Cl, F, CN, CF₃ or OCF₃; in the laterally fluorinated compounds of the formulae I2c, I2d and I2f Y denotes preferably F, Cl or CN.

In the compounds of the formulae I2a, I2b and I2c Y denotes preferably Cl, CF₃ or OCF₃.

The compounds of the formulae I2 include phenyldioxanes without ethyl-linkage of the formulae I2g to I2n:

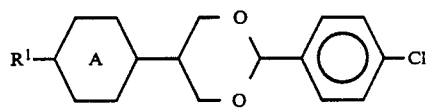

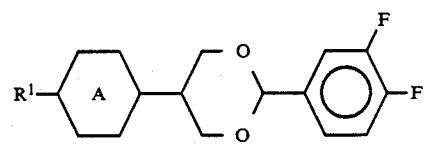

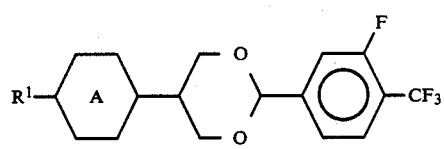

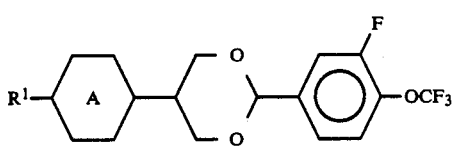

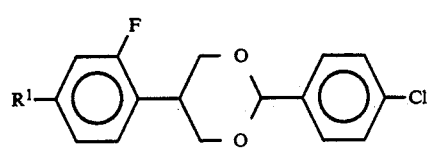

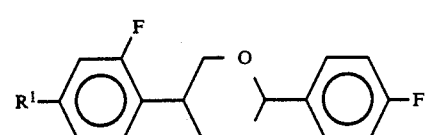

The compounds of the formulae I2g to I2j wherein

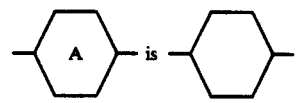

are particularly preferred.

R¹ is preferably alkyl, alkoxy, oxaalkyl or alkenyl and can exhibit a straight-chain or branched structure.

Alkyl or alkoxy preferably are straight-chain and have 2, 3, 4, 5, 6 or 7 C atoms. Accordingly they are preferably ethyl, propyl, butyl, pentyl, hexyl, heptyl, ethoxy, propoxy, butoxy, pentoxy, hexoxy or heptoxy, also methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy. Oxaalkyl is preferably straight-chain 2-oxapropyl (=methoxymethyl), 2-(=ethoxymethyl) or 3-oxybutyl (=2-methoxyethyl), 2-, 3- or 4-oxapentyl, 2-, 3-, 4- or 5-oxahexyl, 2-, 3-, 4-5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8-, or 9-oxadecyl.

In the compounds of these formulae R¹ is preferably alkyl, furthermore also groups in which one CH₂ group is replaced by oxygen.

If R¹ is alkyl and/or alkoxy group, these can be straight-chain or branched. Preferably, they are straight-chain and have 2, 3, 4, 5, 6 or 7 C atoms and are accordingly preferably ethyl, propyl, butyl, pentyl, hexyl, heptyl, ethoxy, propoxy, butoxy, pentoxy, hexoxy or heptoxy, also methyl, octyl, nonyl, methoxy, octoxy or nonoxy.

The compounds of the formula I1a, wherein R¹ is Ethyl, n-Butyl, n-Pentyl or n-Hexyl, are particularly preferred. As a rule they are suitable to lower the threshold voltage of liquid crystal mixtures.

Oxaalkyl is preferably straight-chain 2-oxapropyl (=methoxymethyl), 2-(=ethoxymethyl) or 3-oxybutyl (=2-methoxyethyl), 2-, 3- or 4-oxapentyl, 2-, 3-, 4- or 5-oxahexyl, 2-, 3-, 4-, 5- or 6-oxaheptyl or 2-, 3-, 4-, 5-, 6- or 7-oxaoctyl.

Compounds of the formula I with branched terminal group R¹ can be of importance because of a better solubility in the customary liquid crystal base materials, but in particular as chiral doping substances if they are optically active.

Branched groups of this type as a rule contain not more-than one chain branching. Preferred branched groups are isopropyl, 2-butyl (=1-methylpropyl), isobutyl (=2-methylpropyl), 2-methylbutyl, isopentyl, (=3-methyl- butyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2- methylpentoxy, 3-methylpentoxy, 2-ethylhexoxy, 1-methylhexoxy, 1-methylheptoxy (=2-octyloxy), 2-oxa-3-methylbutyl, 3-oxa-4-methylpentyl, 4-methylhexyl and 6-methyloctoxy.

In the case of compounds with branched terminal groups, formula I includes both the optical antipodes and racemates as well as mixtures thereof.

Of the compounds of the formula I and subformulae thereof, those in which at least one of the radicals contained therein has one of the preferred meanings given are preferred.

The compounds of the formula I are prepared by methods which are known per se, such as are described in the literature (for example in the standard works, such as Houben-Weyl, Methoden der Organischen Chemie Methods of Organic Chemistry, Gerog-Thieme-Verlag, Stuttgart), and in particular under reaction conditions which are known and suitable for the reactions mentioned. Variants which are known per se and are not mentioned in more detail here can also be used in this connection.

If desired, the starting substances can also be formed in situ, such that they are not isolated from the reaction mixture but are immediately reacted further to give the compounds of the formula I.

The preferred synthetic routes are shown in the following schemes I to III:

Scheme I

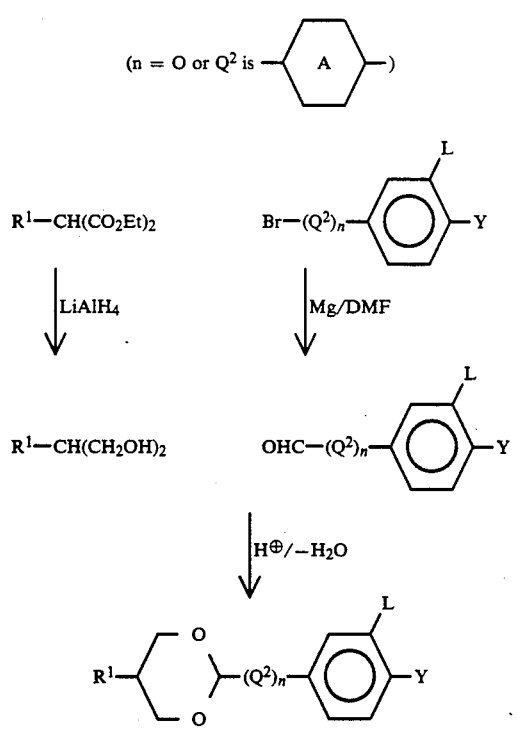

Scheme II

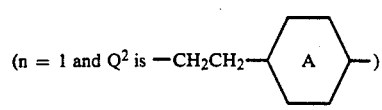

Scheme II
-continued

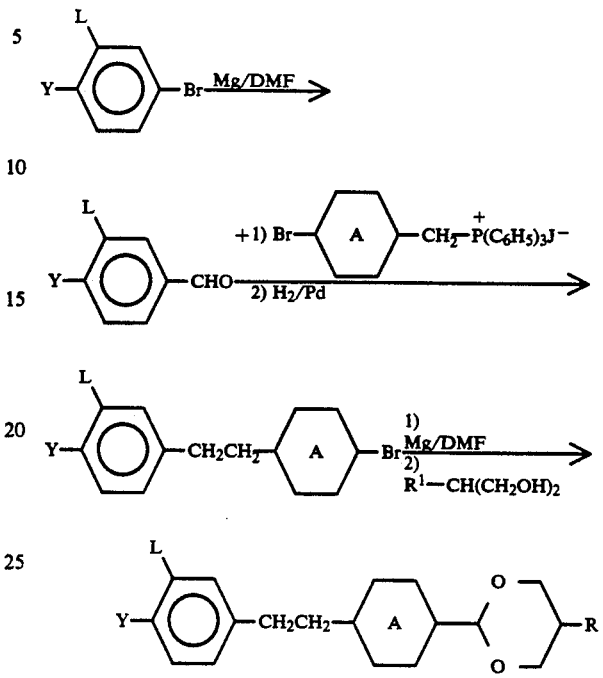

Scheme III

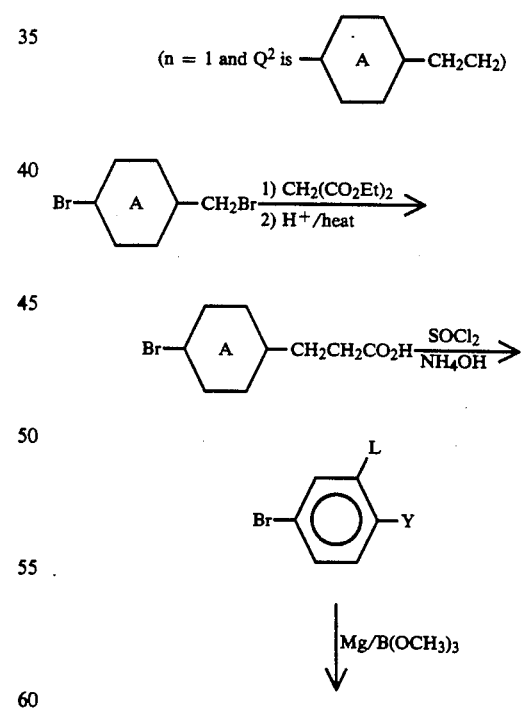

-continued
Scheme III
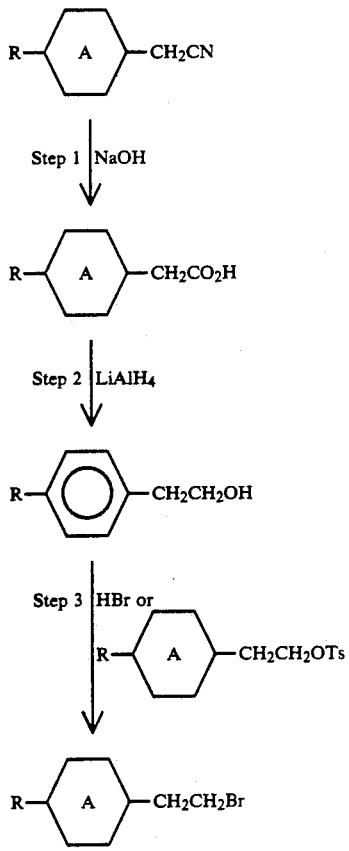
A preferred route for preparation of the ethyl-linked phenyldioxanes of the formula I2 is shown in the following scheme IV:
Scheme IV
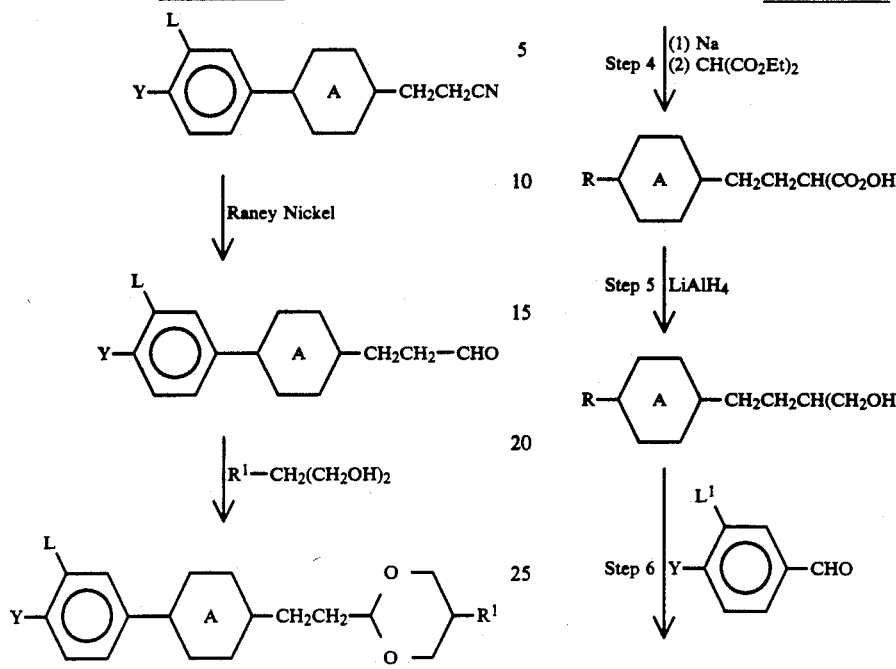
-continued
Scheme IV
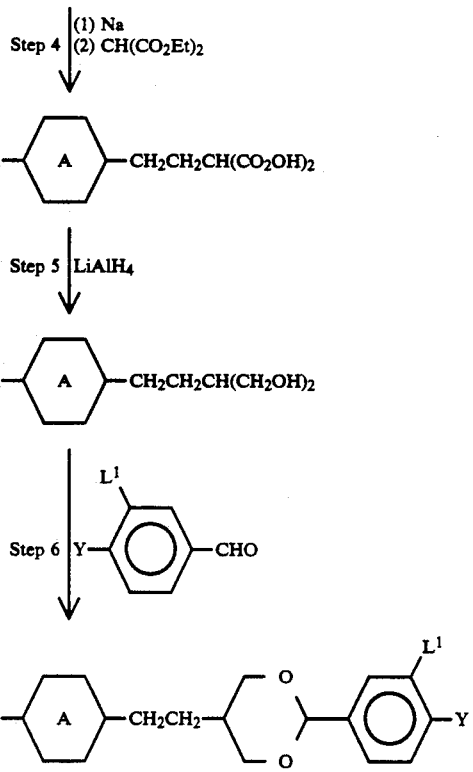
A preferred route for preparation of phenyldioxanes of the formula I2 without ethyl-linkage is shown in the following scheme V:
Scheme V
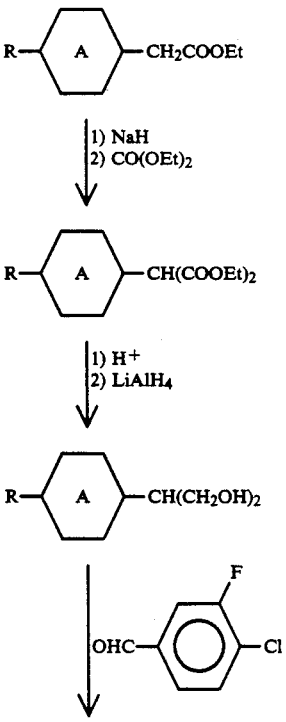

-continued
Scheme V

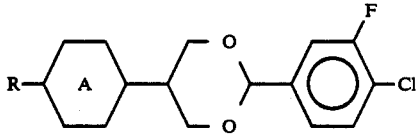

All starting materials are known or prepared in analogy to known starting materials.

All steps are fully conventional and the reaction conditions are known to the skilled worker. The starting materials are known or easily prepared in analogy to known materials.

Other methods of making compounds of formula I are apparent to those skilled in the art.

In addition to one or more compounds of formula I the liquid crystal media according to the invention preferably contain 2-40 components and in particular 4-30 components. Liquid crystal media being composed of one or more compounds of formula I and 7-25 other components are especially preferred.

These additional components are preferably chosen from the nematic or nematogenic (monotropic or isotropic) substances; in particular from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenylbenzoates, cyclohexylphenyl cyclohexanecarboxylates, cyclohexylphenyl cyclohexylcyclohexanecarboxylates, phenylcyclohexanes, cyclohexylbiphenyls, phenylcyclohexyleyclohexanes, cyclohexylcyclohexanes, cyclohexyleyclohexenes, cyclohexylcyclohexylcyclohexene, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclohexyl)-ethanes, 1-cyclohexyl-2-biphenylethanes, 1-phenyl-2-cyclo- hexyl-phenylethanes, optionally halogenated stilbenes, benzyl phenyl ethers, tolanes and substituted cinnamic acids.

The 1,4-phenylene groups of these compounds may be fluorinated.

The most important compounds which are possible constituents of liquid crystal media according to the invention can be characterized by the formulae 1, 2, 3, 4 and 5:

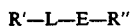  1

  2

  3

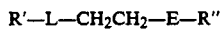  4

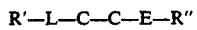  5

In the formulae 1, 2, 3, 4 and 5 L and E may be equal or different from each other. L and E independently from each other denote a bivalent residue selected from the group consisting of —Phe—, —Cyc—, —Phe—Phe—, —Phe—Cyc—, —Cyc—Cyc—, —Pyr—, —Dio—, —G—Phe—, —G—Cyc— and their mirror images; in this compilation of residues Phe denotes unsubstituted or fluorinated 1,4-phenylen, Cyc trans- 1,4-cyclohexylene or 1,4-cyclohexenylen, Pyr pyrimidine-2,5-diyl or pyridine-2,5-diyl, Dio 1,3-dioxane-2,5-diyl and G 2-(trans-1,4-cyclohexyl)-ethyl, pyrimidine-2,5-diyl, pyridine-2,5-diyl or 1,3-dioxane-2,5-diyl.

One of the residues L and E is preferably Cyc, Phe or Pyr. E preferably denotes Cyc, Phe or Phe—Cyc. The liquid crystal media according to the invention preferably contain one or more components selected from the compounds of formulae 1, 2, 3, 4 and 5 with L and E meaning Cyc, Phe and Pyr, said liquid crystal media further containing at the same time one ore more components selected from the compounds of formulae 1, 2, 3, 4 and 5 with one of the residues L and E denoting Cyc, Phe and Pyr and the other residue being selected from the group consisting of —Phe—Phe—, —Phe—Cyc—, —Cyc—Cyc—, —G—Cyc—, said liquid crystal media containing in addition to this optionally one or more components selected from the compounds of formulae 1, 2, 3, 4 and 5 with L and E being selected from the group consisting of —Phe—Cyc—, —Cyc—Cyc—, —G—Phe— and —G—Cyc. In a preferred subgroup of the compounds of formulae 1, 2, 3, 4 and 5 (subgroup 1) R' and R" are independently from each other alkyl, alkenyl, alkoxy, alkenoxy with up to 8 carbon atoms. R' and R" differ from one another in most of these compounds, one of the residues usually being alkyl or alkenyl. In another preferred subgroup of the compounds of formulae 1, 2, 3, 4 and 5 (subgroup 2) R" denotes —CN, —CF$_3$, —OCF$_3$, —OCHF$_2$, —F, —Cl or —NCS while R' has the meaning indicated in subgroup 1 and is preferably alkyl or alkenyl. Other variants of the envisaged substituents in the compounds of formulae 1, 2, 3, 4 and 5 are also customary. Many such substances are commercially available. All these substances are obtainable by methods which are known from the literature or by analogous methods.

The liquid crystal media according to the invention preferably contain in addition to components selected from subgroup 1 also components of subgroup 2, the percentage of these components being as follows:

subgroup 1: 20 to 90%, in particular 30 to 90%
subgroup 2: 10 to 50%, in particular 10 to 50%

In these liquid crystal media the percentages of the compounds according to the invention and the compounds of subgroup 1 and 2 may add up to give 100%.

The media according to the invention preferably contain 1 to 40%, in particular 5 to 30% of the compounds according to the invention. Media containing more than 40%, in particular 45 to 90% of the compounds according to the invention are further preferred. The media contain preferably 3, 4 or 5 compounds according to the invention.

The media according to the invention are prepared in a manner which is customary per se. As a rule, the components are dissolved in one another, advantageously at elevated temperature. The liquid crystal media according to the invention can be modified by suitable additives so that they can be used in all the types of liquid crystal display devices. Such additives are known to the expert and are described in detail in the literature (H. Kelker/R. Hatz, Handbook of Liquid Crystals, Verlag Chemie, Weinheim, 1980). For example, it is possible to add pleochroic dyestuffs to prepare colored guest-host systems or substances for modifying the dielectric anisotropy, the viscosity and/or the orientation of the nematic phases.

The following examples are to be construed as merely illustrative and not limitative. m.p.=melting point, c.p.=clearing point. In the foregoing and in the following all parts and percentages are by weight and the temperatures are set forth in degrees Celsius. "Customary work-up" means that water is added, the mixture is extracted with methylene chloride, the organic phase is separated off, dried and evaporated, and the product is purified by crystallization and/or chromatography.

EXAMPLE 1

According to Scheme I given above 4-(5-propyldioxan-2-yl)-chlorobenzene is obtained from p-bromochlorobenzene and 2-(hydroxymethyl)-pentan-1-ol, C 72 I, $\Delta\epsilon = 8.6$.

EXAMPLES 2 TO 20

The following compounds are prepared analogously

| | $R^1$ | n | $Q^2$ | L | Y |
|---|---|---|---|---|---|
| (2) | $C_5H_{11}$ | 0 | — | H | Cl, K 66 I, $\Delta\epsilon = 7.0$ |
| (3) | $C_7H_{15}$ | 0 | — | H | Cl |
| (4) | $C_3H_7$ | 0 | — | F | Cl, C 33 I, $\Delta\epsilon = +11.8$ |
| (5) | $C_5H_{11}$ | 0 | — | F | Cl, C 30 I, $\Delta\epsilon = 9.5$ |
| (6) | $C_7H_{15}$ | 0 | — | F | Cl |
| (7) | $C_3H_7$ | 0 | — | F | F |
| (8) | $C_5H_{11}$ | 0 | — | H | F, C 25 I, $\Delta\epsilon = +7.7$ |
| (9) | $C_7H_{15}$ | 0 | — | H | F, C 15 I, $\Delta\epsilon = +6.9$ |
| (10) | $C_3H_7$ | 1 | phenylene | H | Cl |
| (11) | $C_5H_{11}$ | 1 | phenylene | H | Cl |
| (12) | $C_7H_{15}$ | 1 | phenylene | H | Cl |
| (13) | $C_3H_7$ | 1 | phenylene | F | Cl |
| (14) | $C_3H_7$ | 1 | phenylene | H | F |
| (15) | $C_2H_5$ | 0 | — | H | Cl |
| (16) | $C_4H_9$ | 0 | — | H | Cl |
| (17) | $C_6H_{13}$ | 0 | — | H | Cl |
| (18) | $C_3H_7$-cyclohexyl- | 0 | — | F | Cl C 96 N 142 I, $\Delta\epsilon = 10.3$ |
| (19) | $C_3H_7$ | 1 | cyclohexylene (H) | H | Cl |
| (20) | $C_5H_{11}$ | 1 | cyclohexylene (H) | H | Cl |

Further are:
C: crystalline-solid state, S: smectic phase (the index denoting the typ of smetic phase), N: nematic phase, Ch: cholesteric phase, I: isotropic phase. The number being embraced by 2 of these symbols denotes the temperature of phase change.

EXAMPLE 21

According to Scheme II given above 1-(4-chloro-3-fluorophenyl)-2-(4-(5-propyldioxane-2-yl)-phenyl)-ethane is obtained from 1-(4-chloro-3-fluorophenyl)-2-

(4-bromophenyl)-ethane and 2-(hydroxymethyl)-pentan-1-ol.

EXAMPLES 22 TO 24

The following compounds are obtained analogously

|  | R¹ | n | Q² | L | Y |
|---|---|---|---|---|---|
| (22) | $C_5H_{11}$ | 1 | —⟨◯⟩—CH₂CH₂— | F | Cl |
| (23) | $C_5H_{11}$ | 1 | —⟨◯⟩—CH₂CH₂— | H | Cl |
| (24) | $C_5H_{11}$ | 1 | —⟨◯⟩—CH₂CH₂— | F | F |

EXAMPLE 25

According to Scheme III given above 1-(4'-chloro-3'-fluorobiphenyl-4-yl)-2-(5-propyldioxane-2-yl)-ethane is obtained from 3-(4'chloro-3'-fluorobiphenyl-4-yl)-proponaldehyde and 2-(hydroxymethyl)-pentan-2-ol.

EXAMPLES 26 TO 28

The following compounds obtained analogously:

|  | R¹ | n | Q² | L | Y |
|---|---|---|---|---|---|
| (26) | $C_5H_{11}$ | 1 | —CH₂CH₂—⟨◯⟩— | F | Cl |
| (27) | $C_5H_{11}$ | 1 | —CH₂CH₂—⟨◯⟩— | H | Cl |
| (28) | $C_5H_{11}$ | 1 | —CH₂CH₂—⟨◯⟩— | F | F |

EXAMPLE 29

Mixture (A) contains:

22% $C_3H_7$—⟨⬡⟩—⟨◯⟩—$C_2H_5$

20% $C_3H_7$—⟨⬡⟩—⟨◯⟩—$OCH_3$

15% $C_3H_7$—⟨⬡⟩—⟨◯⟩—$OC_2H_3$

19% $C_3H_7$—⟨⬡⟩—⟨◯⟩—⟨◯⟩—$C_2H_3$

14% $C_5H_{11}$—⟨⬡⟩—⟨◯⟩—⟨◯⟩—$C_2H_3$

5% $C_3H_7$—⟨⬡⟩—⟨◯⟩—⟨◯⟩—⟨⬡⟩—$C_3H_7$

5% $C_3H_7$—⟨⬡⟩—⟨◯⟩—⟨◯⟩—⟨⬡⟩—$C_5H_{11}$ and exhibits N 72 I, Δε+0.06, n=0.1139

Mixture (B) contains 90% of mixture (A) and 10% of

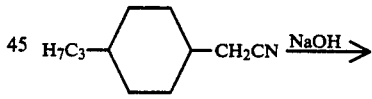

and exhibits N 65.2 I, Δε= +1.04, Δn=0.1097.

EXAMPLE 30

Mixture (C) contains 90% of mixture (A) and 10% of

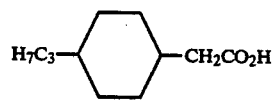

and exhibity N 60.1 I, Δε= +1.24, Δn=0.1076.

EXAMPLE 31

Preparation of 1(trans-4-Propylcyclohexyl)-2-[-(4-chlorophenyl)-dioxane-5-yl]-ethane

Step One $H_7C_3$—⟨⬡⟩—$CH_2CN$ $\xrightarrow{NaOH}$ $H_7C_3$—⟨⬡⟩—$CH_2CO_2H$ The trans-4-propylcyclohexylmethyleyanide (0.1 mole), NaOH (0.39 moles) and water (20 ml) are refluxed in digol (100 ml) for 30 hours. The reaction mixture is added, at 50° C., to water acidified and the product extracted into dichloromethane. The combined organic layers are washed with water, dried and the solvent removed. The crude acid is recrystallised from 7 vols of petrol ether (60–80~).

Step Two $H_7C_3$—⟨⬡⟩—$CH_2CO_2H$ $\xrightarrow{LiAlH_4}$

-continued
Step Two

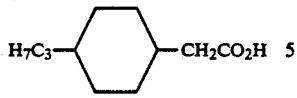

A solution of the 2-(trans-4-propyleyclohexyl)- acetic acid (0.1 moles) of STEP 1 in ether (8.0 moles) is slowly added to a mixture of LiAlH₄ (0.211 moles) in dry ether (200 ml) at such a rate to give a gentle reflux. The mixture is then stirred for a further 3 hours. Excess LiAlH₄ is destroyed with ethyl acetate: ether (1:1) at 10° C. Dilute HCl is added and the product extracted into ether, washed with water and dried. After removal of the solvent the product was distilled under high vacuum.

Step Three

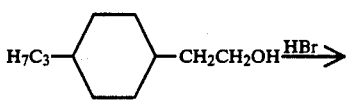

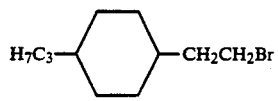

The (2-trans-4-propylcyclohexyl)-ethyl alcohol (0.1 moles) is refluxed in a mixture of HBr (50 ml) and H₂SO₄ (10 ml). Water is added and the product extracted into dichloromethane. The crude bromide is distilled under high vacuum.

Step Four

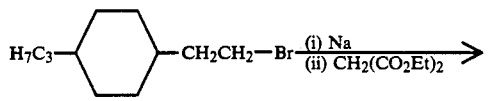

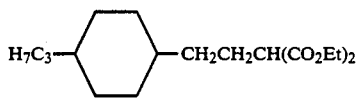

To a solution of sodium ethoxide (made from Na in 70 ml IMS) is added diethyl malonate (0.105 moles), followed by the 2-(trans-4-propylcyclohexyl)-ethyl bromide (0.1 moles) of Step Three at 50° C. The mixture is refluxed for 4 hours and then the solvent removed. Water is added and the product extracted into ether and purified by distillation.

Step Five

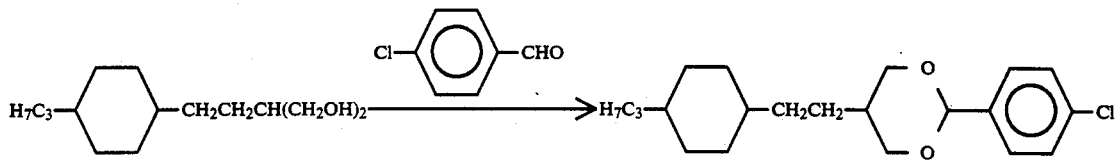

The 2-(trans-4-propylcyclohexyl)-ethyl (0.1 moles) of STEP 3 in THF (50 ml) is slowly added to LiAlH₄ (0.114 moles) in THF (75 ml) at 40° C. under nitrogen. The mixture is refluxed for a further 4 hours and the excess LiAlH₄ is destroyed with dilute solution of water in THF. Sodium carbonate (12 g) in water (35 ml) is added at 80° C. After cooling to room temperature the solids are removed by filtration and the solvent removed. The product is then distilled under high vacuum.

Step Six

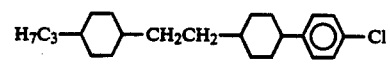

The 4-(trans-4-propylcyclohexyl)-2-(hydroxymethyl)-butane-2-ol (0.1 moles of STEP 5 is refluxed in toluene (220 ml) with the p-chloro-benzaldehyde (0.1 moles) and toluene sulphonic acid (0.8 g). Water being removed using a Dean Stark apparatus. After 3 hours at reflux the mixture is cooled and washed wit aq. NaHCO₃ then water, dried and the solvent evaporated. The crude product is chromatographed over silica gel and recrystallised from methanol.

EXAMPLES 32 TO 48

In place of the used trans-4-propylcyclohexylmethyl-cyanide and the p-chloro-benaldehyde other homologues cyclohexylmethyleyanides and benzaldehydes can be used for preparation of the following compounds in analogy to example 25:

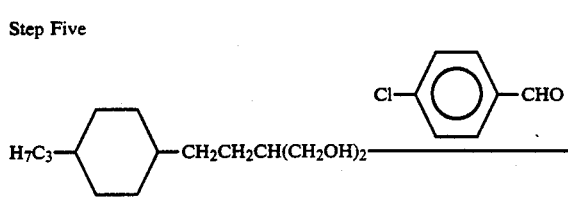

| n | L¹ | Y |
|---|---|---|
| (32) | 5 | H | Cl |
| (33) | 7 | H | Cl |
| (34) | 3 | F | Cl |
| (35) | 5 | F | Cl |
| (36) | 7 | F | Cl |
| (37) | 3 | F | F |
| (38) | 5 | F | F |
| (39) | 7 | F | F |
| (40) | 5 | H | OCF₃ |
| (41) | 5 | H | CF₃ |
| (42) | 5 | H | CN |
| (43) | 5 | H | F |
| (44) | 5 | F | OCF₃ |
| (45) | 5 | F | CF₃ |
| (46) | 3 | F | CN |
| (47) | 5 | F | CN |
| (48) | 7 | F | CN |

EXAMPLE 49

Preparation of 1-(4-Pentyloxyphenyl)-2-[2-(4-cyanophenyl)]-ethane

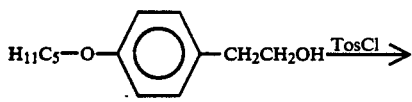

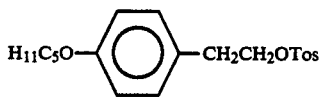

The 2-(4-Pentyloxyphenyl)-ethanol (0.1 moles/obtained from benzylcyanide in an analogous way to Example 1 STEP 1/2) is stirred in pyridine (35 ml) and toluene sulphonyl chloride (0.125 moles). Dilute HCl is added and the product is filtered under vacuum, washed with water and recrystallised from 2 volumes of methanol at 3° C.

Step Two

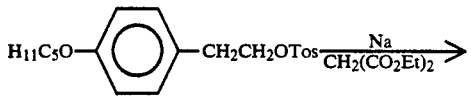

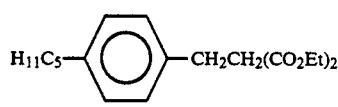

To a solution of sodium methoxide (made from Na in 7o ml (MS) is added diethyl malenate (0.105 moles), followed by the tosylate of STEP 1 (0.1 moles). The product is obtained analogously to Example 1 STEP 4.

Step Three

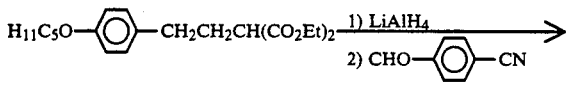

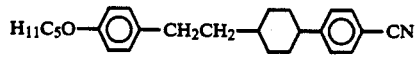

The diester (0.1 moles) of STEP 2 is reduced with LiAlH$_4$, analogously to Example 1 STEP 5 and condensed with p-formylbenzonitrile (0.1 moles) with toluene sulphonic acid in a Dean and Stark trap in analogy to Example 1 STEP 6.

EXAMPLES 50 TO 70

In place of the used 2-(4-pentyloxyphenyl)-ethanol and p-formylbenzonitrile other homologue 2-phenylethanoles and benzaldehydes can be used for preparation of the following compounds in analogy to example 43:

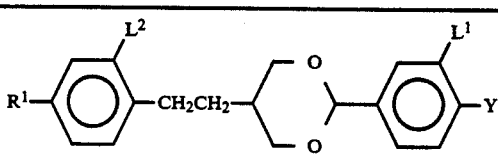

| Example | R$^1$ | L$^1$ | L$^2$ | Y |
|---|---|---|---|---|
| (50) | H$_7$C$_3$ | H | H | CN |
| (51) | H$_{11}$C$_5$ | H | H | CN |
| (52) | H$_7$C$_3$O | F | H | CN |
| (53) | H$_{11}$C$_5$ | F | H | CN |
| (54) | H$_{11}$C$_5$ | H | F | CN |
| (55) | H$_{11}$C$_5$O | H | H | F |
| (56) | H$_7$C$_3$ | H | H | F |
| (57) | H$_7$C$_3$O | H | H | F |
| (58) | H$_{11}$C$_5$ | F | H | F |
| (59) | H$_{11}$C$_5$ | H | F | F |
| (60) | H$_9$C$_4$O | H | H | Cl |
| (61) | H$_7$C$_3$ | H | H | Cl |
| (62) | H$_{11}$C$_5$ | H | H | Cl |
| (63) | H$_7$C$_3$O | H | H | Cl |
| (64) | H$_{11}$C$_5$ | F | H | Cl |
| (65) | H$_{11}$C$_5$ | H | F | Cl |
| (66) | H$_{11}$C$_5$ | H | H | OCF$_3$ |
| (67) | H$_{11}$C$_5$ | H | H | CF$_3$ |
| (68) | H$_{11}$C$_5$ | H | F | OCF$_3$ |
| (69) | H$_{11}$C$_5$ | F | H | CF$_3$ |
| (70) | H$_{11}$C$_5$ | F | H | OCF$_3$ |

EXAMPLE 71

Mixture (D) contains

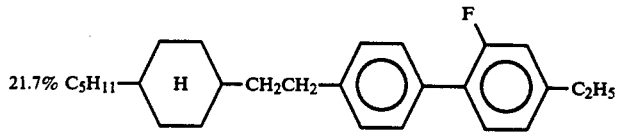

21.7%

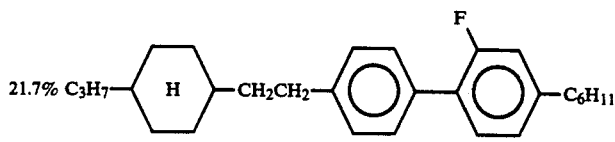

21.7%

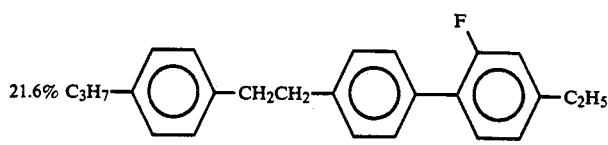

21.6%

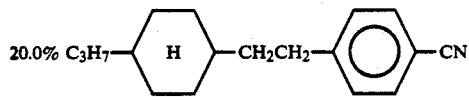
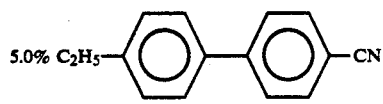
and
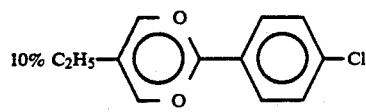
and exhibits N 69.1 I, $V_{90}$ 2.24 Volt (measured in a 90° TN cell).
EXAMPLE 72
Mixture (E) contains
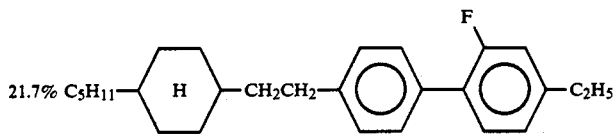
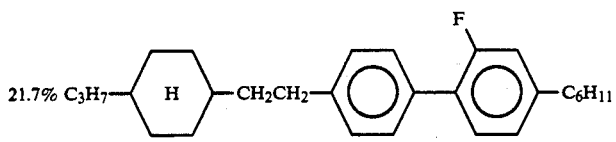
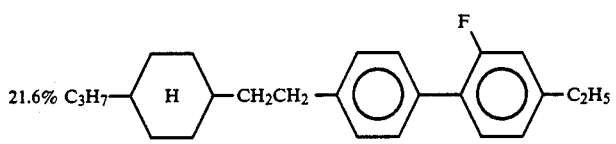
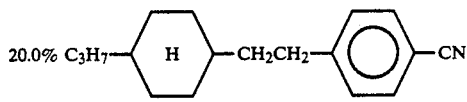
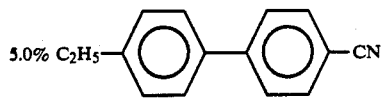
and
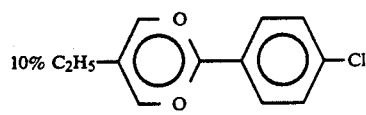
and exhibits N 71 I, $V_{90}$ 2.37 Volt (measured in a 90° TN cell).
EXAMPLE 73
Mixture (F) contains
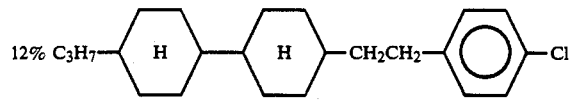

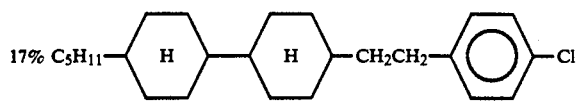 17% C$_5$H$_{11}$—H—H—CH$_2$CH$_2$—⬡—Cl

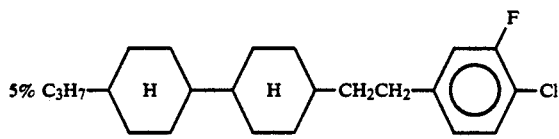 5% C$_3$H$_7$—H—H—CH$_2$CH$_2$—⬡(F)—Cl

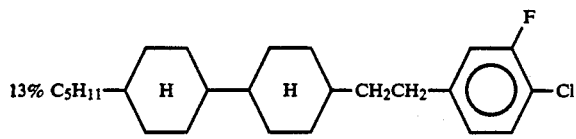 13% C$_5$H$_{11}$—H—H—CH$_2$CH$_2$—⬡(F)—Cl

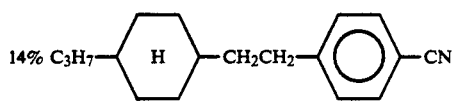 14% C$_3$H$_7$—H—CH$_2$CH$_2$—⬡—CN

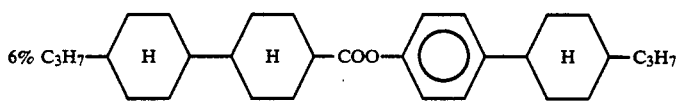 6% C$_3$H$_7$—H—H—COO—⬡—H—C$_3$H$_7$

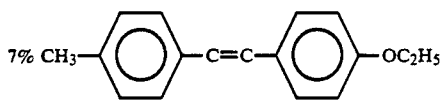 7% CH$_3$—⬡—C≡C—⬡—OC$_2$H$_5$

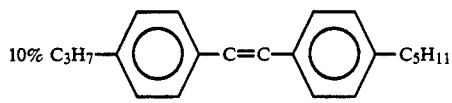 10% C$_3$H$_7$—⬡—C≡C—⬡—C$_5$H$_{11}$

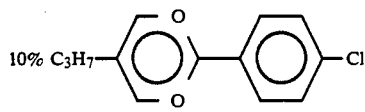 10% C$_3$H$_7$—(dioxane)—⬡—Cl

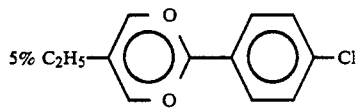 5% C$_2$H$_5$—(dioxane)—⬡—Cl and exhibits

N 94 I, η 19.6 cSt, Δn 0.139 and V$_{90}$ of 2.809 Volts in a 240° STN cell.

We claim:

1. A phenyldioxane of formula I

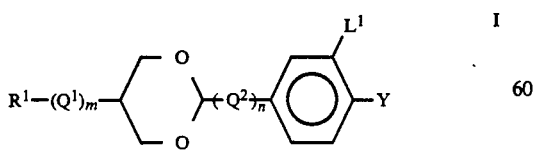

wherein
R$^1$ is alkyl residue with up to 16 C atoms, wherein one or two nonadjacent CH$_2$ groups may be replaced by —O—, —S—, —CO—O—, or —O—CO—,
Q$^1$ and Q$^2$ are each independently

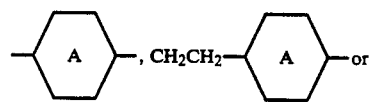

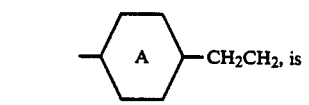

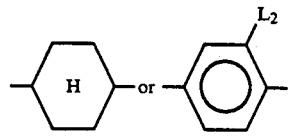

L$^1$ and L$^2$ are each independently F or H, and
Y is Cl or F
m and n are 0 or 1 with the provisos that
 a) in the case that m is 0, m is 1 and $Q^1$ is

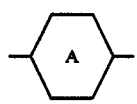

one of $L^1$ and $L^2$ is F and Y is Cl or F and
 b) in the case that n is 1, m is 0 and $Q^2$ is

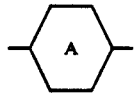

one of $L^1$ and $L^2$ is F or $L^1$ and $L^2$ are H and Y is Cl.

2. A phenyldioxane according to claim 1 wherein m is O and Y is Cl or in the case that $L^1$ or $L^2$ is F also F.

3. A phenyldioxane according to claim 1 wherein n is O, m is 1 and $Q^1$ is

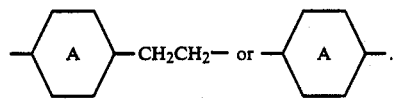

4. A phenyldioxane of claim 2 wherein $R^1$ have the meaning given,
$Q^2$ is

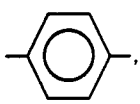

n is 1, and
Y is Cl.

5. A phenyldioxane according to claim 3 wherein $R^1$, $L^1$ and $L^2$ have the meaning given,

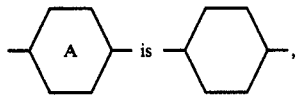

and Y is Cl.

6. A phenyldioxane according to claim 1 of the part formulae I1a to I1h:

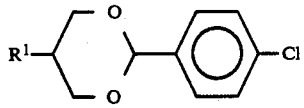
I1aa

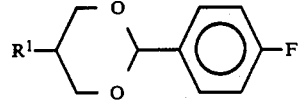
I1ab

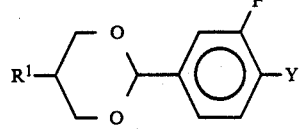
I1b

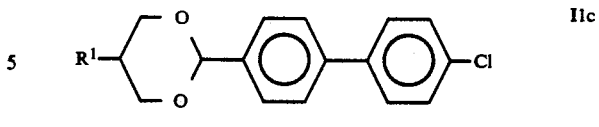
I1c

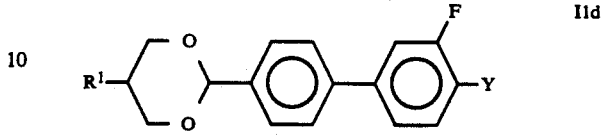
I1d

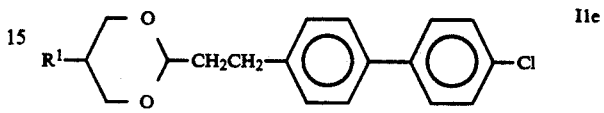
I1e

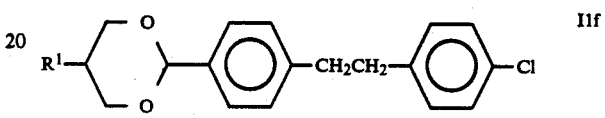
I1f

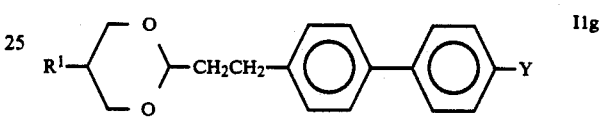
I1g or

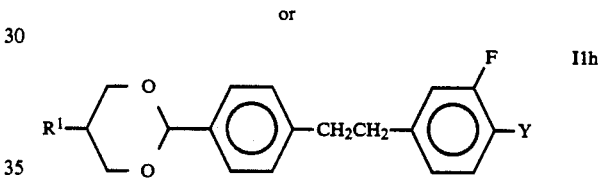
I1h

7. A phenyldioxane according to claim 1 of the part formulae I2a to I2f:

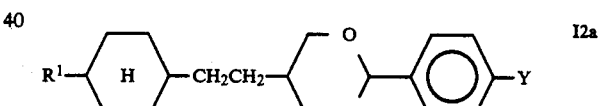
I2a

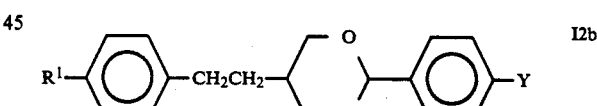
I2b

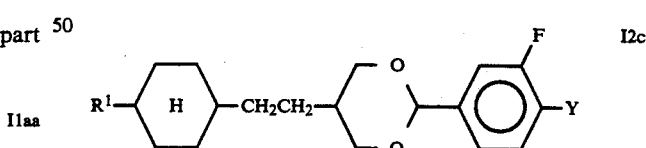
I2c

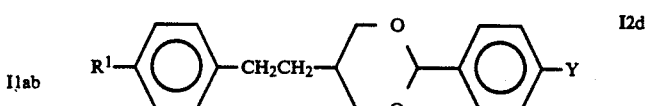
I2d

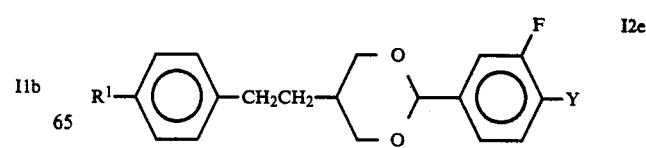
I2e or

-continued
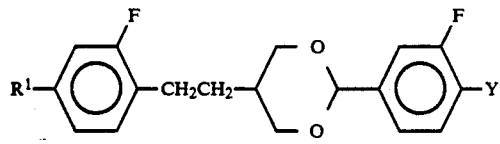
I2f
8. A phenyldioxane according to claim 7 of the part formulae I2a to I2c, wherein Y is Cl.
9. A phenyldioxane according to claim 1 of the part formulae I2g, I2h, I2k or I2l:
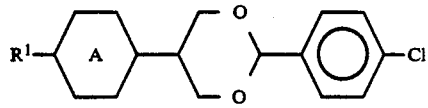
I2g
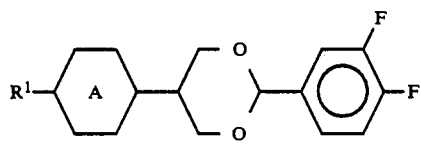
I2h
-continued
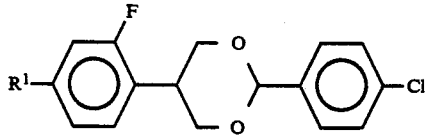
I2k
or
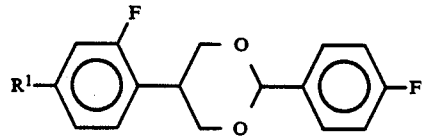
I2l
10. A phenyldioxane according to claim 9 or the part formulae I2g or I2h, wherein
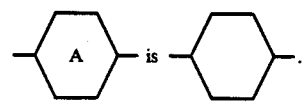
* * * * *